US008491591B2

(12) United States Patent
Fürderer

(10) Patent No.: US 8,491,591 B2
(45) Date of Patent: Jul. 23, 2013

(54) DEVICE FOR STRAIGHTENING AND STABILIZING THE VERTEBRAL COLUMN

(75) Inventor: Sebastian Fürderer, Mainz (DE)

(73) Assignee: DePuy Synthes Products, LLC, Raynham, MA (US)

( * ) Notice: Subject to any disclaimer, the term of this patent is extended or adjusted under 35 U.S.C. 154(b) by 472 days.

(21) Appl. No.: 12/268,215

(22) Filed: Nov. 10, 2008

(65) Prior Publication Data
US 2009/0069850 A1 Mar. 12, 2009

Related U.S. Application Data

(62) Division of application No. 10/286,458, filed on Nov. 1, 2002, now abandoned.

(51) Int. Cl.
A61B 17/58 (2006.01)
(52) U.S. Cl.
USPC .......................................... 606/92; 606/86 R
(58) Field of Classification Search
USPC ............... 606/99, 86 A, 92–94, 90, 86 R, 79, 606/85, 279; 623/17.11–17.16
See application file for complete search history.

(56) References Cited

U.S. PATENT DOCUMENTS

| | | |
|---|---|---|
| 2,381,050 A | 12/1943 | Hardinge |
| 3,701,703 A | 10/1972 | Zimmer et al. |
| 4,055,029 A | 10/1977 | Kalbow et al. |
| 4,820,349 A | 4/1989 | Saab |
| 4,969,888 A | 11/1990 | Scholten et al. |
| 5,041,114 A | 8/1991 | Chapman et al. |
| 5,059,193 A | 10/1991 | Kuslich |
| 5,108,404 A | 4/1992 | Scholten et al. |
| 5,192,326 A | 3/1993 | Bao et al. |
| 5,390,683 A | 2/1995 | Pisharodi |
| 5,443,496 A | 8/1995 | Schwartz et al. |
| 5,549,679 A | 8/1996 | Kuslich |
| 5,599,301 A | 2/1997 | Jacobs et al. |
| 5,601,593 A | 2/1997 | Freitag |
| 5,693,100 A | 12/1997 | Pisharodi |
| 5,707,390 A | 1/1998 | Bonutti |

(Continued)

FOREIGN PATENT DOCUMENTS

| | | |
|---|---|---|
| EP | 0 493 789 | 12/1991 |
| WO | WO 98/56301 | 12/1998 |

(Continued)

OTHER PUBLICATIONS

Jensen, Mary E., et al., "Percutaneous Polymethylmethacrylate Vertebroplasty in the Treatment of Osteoporotic Vertebral Body Compression Fractures: Technical Aspects"., AJNR: 18, Nov. 1997.

(Continued)

Primary Examiner — Nicholas Woodall
Assistant Examiner — Melissa A Hall
(74) Attorney, Agent, or Firm — Stradley Ronon Stevens & Young, LLP

(57) ABSTRACT

A device for straightening and stabilizing the vertebral column, particularly for stabilizing broken vertebrae, includes a supporting implant which is plastically expandable by internal pressure. The supporting implant can be placed into the interior of a vertebral body which has been fractured under compression or between adjacent vertebral bodies. A pressure balloon to which pressure fluid can be admitted may be arranged in the interior of the supporting implant for producing the internal pressure.

13 Claims, 2 Drawing Sheets

U.S. PATENT DOCUMENTS

| | | | |
|---|---|---|---|
| 5,759,191 | A | 6/1998 | Barbere |
| 5,827,289 | A | 10/1998 | Reiley et al. |
| 5,893,850 | A | 4/1999 | Cachia |
| 5,972,015 | A | 10/1999 | Scribner et al. |
| 6,096,038 | A | 8/2000 | Michelson |
| 6,127,597 | A * | 10/2000 | Beyar et al. ............... 606/86 R |
| 6,179,856 | B1 | 1/2001 | Barbere |
| 6,235,043 | B1 | 5/2001 | Reiley et al. |
| 6,241,734 | B1 * | 6/2001 | Scribner et al. ............... 606/93 |
| 6,248,110 | B1 * | 6/2001 | Reiley et al. ............... 606/93 |
| 6,306,177 | B1 | 10/2001 | Felt et al. |
| 6,395,032 | B1 | 5/2002 | Gauchet |
| 6,440,138 | B1 | 8/2002 | Reiley et al. |
| 6,478,800 | B1 | 11/2002 | Fraser et al. |
| 6,558,390 | B2 | 5/2003 | Cragg |
| 6,613,054 | B2 | 9/2003 | Scribner et al. |
| 6,620,162 | B2 | 9/2003 | Kuslich et al. |
| 6,632,235 | B2 | 10/2003 | Weikel et al. |
| 6,663,647 | B2 | 12/2003 | Reiley et al. |
| 6,679,886 | B2 | 1/2004 | Weikel et al. |
| 6,706,069 | B2 | 3/2004 | Berger |
| 6,716,216 | B1 | 4/2004 | Boucher et al. |
| 6,719,761 | B1 | 4/2004 | Reiley et al. |
| 6,726,691 | B2 | 4/2004 | Osorio et al. |
| 6,733,532 | B1 | 5/2004 | Gauchet et al. |
| 6,740,093 | B2 | 5/2004 | Hochschuler et al. |
| 6,863,672 | B2 | 3/2005 | Reiley et al. |
| 6,899,719 | B2 | 5/2005 | Reiley et al. |
| 6,981,981 | B2 | 1/2006 | Reiley et al. |
| 7,025,771 | B2 | 4/2006 | Kuslich et al. |
| 7,044,954 | B2 | 5/2006 | Reiley et al. |
| 7,097,648 | B1 | 8/2006 | Globerman et al. |
| 7,153,307 | B2 | 12/2006 | Scribner et al. |
| 7,166,121 | B2 | 1/2007 | Reiley et al. |
| 7,226,481 | B2 | 6/2007 | Kuslich |
| 7,241,303 | B2 | 7/2007 | Reiss et al. |
| 7,261,720 | B2 | 8/2007 | Stevens et al. |
| 2002/0026195 | A1 * | 2/2002 | Layne et al. ............... 606/72 |
| 2002/0058947 | A1 | 5/2002 | Hochschuler et al. ........ 606/94 |
| 2002/0068974 | A1 * | 6/2002 | Kuslich et al. ............. 623/17.11 |
| 2003/0050702 | A1 * | 3/2003 | Berger ...................... 623/17.12 |
| 2003/0130664 | A1 * | 7/2003 | Boucher et al. ............. 606/86 |
| 2003/0220649 | A1 * | 11/2003 | Bao et al. ................... 606/90 |
| 2004/0073308 | A1 | 4/2004 | Kuslich et al. |
| 2004/0097930 | A1 | 5/2004 | Justis et al. |
| 2004/0102774 | A1 | 5/2004 | Trieu |
| 2004/0167625 | A1 | 8/2004 | Beyar et al. |
| 2004/0210297 | A1 | 10/2004 | Lin et al. |
| 2004/0215343 | A1 | 10/2004 | Hochschuler et al. |
| 2004/0215344 | A1 | 10/2004 | Hochschuler et al. |
| 2004/0220615 | A1 | 11/2004 | Lin et al. |
| 2005/0070911 | A1 | 3/2005 | Carrison et al. |
| 2005/0143827 | A1 | 6/2005 | Globerman et al. |
| 2005/0234498 | A1 | 10/2005 | Gronemeyer et al. |
| 2006/0079905 | A1 | 4/2006 | Beyar et al. |
| 2006/0100706 | A1 | 5/2006 | Shadduck et al. |
| 2006/0190083 | A1 | 8/2006 | Arnin et al. |
| 2006/0271061 | A1 | 11/2006 | Beyar et al. |
| 2006/0293750 | A1 | 12/2006 | Sherman et al. |
| 2007/0055266 | A1 | 3/2007 | Osorio et al. |
| 2007/0055267 | A1 | 3/2007 | Osorio et al. |
| 2007/0055280 | A1 | 3/2007 | Osorio et al. |
| 2007/0055284 | A1 | 3/2007 | Osorio et al. |
| 2007/0055285 | A1 | 3/2007 | Osorio et al. |
| 2007/0282443 | A1 | 12/2007 | Globerman et al. |

FOREIGN PATENT DOCUMENTS

| | | |
|---|---|---|
| WO | WO 01/76514 | 10/2001 |
| WO | WO 02/43628 | 6/2002 |
| WO | WO 03/007853 | 1/2003 |
| WO | WO 2005/048856 | 6/2005 |

OTHER PUBLICATIONS

Gangi, Afshin, et al., "Percutaneous Vertebroplasty Guided by a Combination of CT and Fluoroscopy"., AJNR 15:83-86, Jan. 1994.

Cotten, Anne., MD., et al. "Percutaneous Vertebroplasty for Osteolytic Metastases and Myeloma: Effects of the Percentage of Lesion Filling and the Leakage of Methyl Methacrylate at Clinical Follow-up"., Radiology 1996; 200:525-530.

Cotten, Anne, et al., "Preoperative Percutaneous Injection of Methyl Methacrylate and N-Butyl Cyanoacrylate in Vertebral Hemangiomas"; AJNR 17:137-142 (1996).

Maciunas, Robert J., MD., "Endovascular Neurological Intervention"; American Association of Neurological Surgeons; 153-158.

* cited by examiner

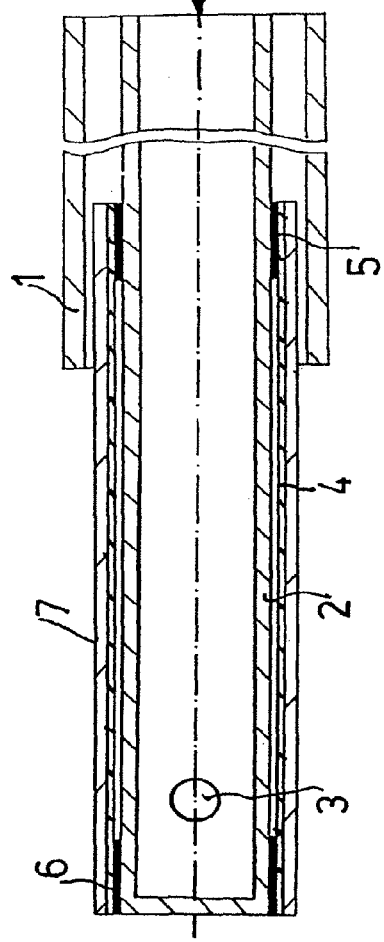
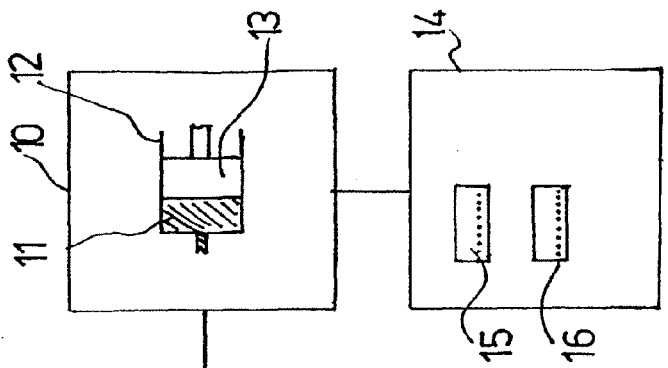
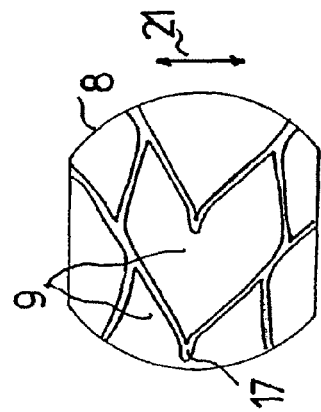
FIG.2
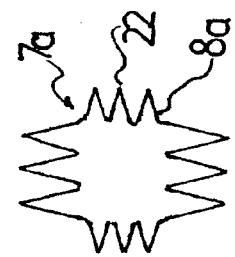
FIG.5
FIG.1

DEVICE FOR STRAIGHTENING AND STABILIZING THE VERTEBRAL COLUMN

CROSS-REFERENCE TO RELATED APPLICATIONS

This application is a division of U.S. patent application No. 10/286,458, filed Nov. 01, 2002 now abandoned, which claims the benefit of German Patent Application No. DE 101 54 163.5, filed Nov. 3, 2001, the entire disclosures of which are incorporated herein by reference.

BACKGROUND OF THE INVENTION

1. Field of the Invention

The present invention relates to a device for straightening and stabilizing the vertebral column, particularly for stabilizing broken vertebrae.

2. Description of the Related Art

Devices for straightening and stabilizing broken vertebrae are known to be used. These devices include a catheter which can be inserted into the interior of the vertebra through a duct drilled into the pedicle of the broken vertebra. A pressure line pushed through the catheter into the interior of the vertebra has at the end thereof an expandable pressure balloon which makes it possible to expand once again and return into its original shape a vertebra which has been compressed and possibly broken. The balloon which has subsequently been decompressed and pulled out together with the pressure line leaves a hollow space into which a bone filler material can be introduced through the catheter.

SUMMARY OF THE INVENTION

It is the primary object of the present invention to provide a novel device for stabilizing the vertebral column, particularly for straightening and stabilizing broken vertebrae, which makes it possible to achieve a higher degree of stabilization more quickly than by using the known devices, wherein the required operation is simpler.

In accordance with the present invention, the device for straightening and stabilizing the vertebral column is characterized by a supporting implant which is plastically expandable by internal pressure.

Such a supporting implant, which is preferably provided for being arranged in the interior of a vertebral body fractured under compression or also, for example, after an intervertebral disc resection for arrangement between adjacent vertebral bodies, can be easily moved to the implantation location because of its small dimensions. After the expansion has been effected, a preliminary stabilization is ensured immediately because the supporting implant maintains its final shape obtained during the plastic expansion. A filler material which is initially present in liquid form can be introduced under slight pressure into the created hollow space and can harden in the hollow space. Because of the action of the supporting implant, it is not necessary to wait until the filler material has hardened completely.

While mechanical tools for producing the internal pressure are conceivable, a preferred embodiment of the invention provides for a device which produces the internal pressure by means of a pressure fluid.

The pressure fluid can be introduced directly into the supporting implant, which requires that the supporting implant and the supply connections are pressure tight. However, in accordance with a preferred embodiment, a pressure balloon is provided which is arranged in the interior of the supporting implant and into which the pressure fluid can be introduced.

The expandable supporting implant may include a weakened wall, or a wall which is perforated in the manner of expanded metal and/or folded in the manner of a bellows.

This type of supporting implant can be expanded with relatively low internal pressure, wherein the stability of the expanded implant is reduced by the weakened or folded portions, however, the implant can still carry out a sufficient supporting function.

The wall of the expandable supporting implant may have weak portions and/or folds arranged in such a way that the supporting implant expands into a desired shape. For example, if such a supporting implant is arranged between adjacent vertebrae, the desired shape is approximately that of a parallelepiped.

In accordance with a preferred embodiment of the invention, the expandable supporting implant has an oblong shape so that it is suitable for being arranged at the implantation location by means of a catheter or a guide sleeve. In particular, the expandable supporting implant, and possibly the pressure balloon, may be placed in the manner of a stocking on a pressure line which can be introduced through the guide sleeve, wherein the pressure balloon is arranged between the supporting implant and the pressure line and, in the non-expanded state, forms a hose-type sleeve which surrounds the pressure line and which is connected at its ends in a pressure-tight manner by being placed around the circumference of the pressure line.

The pressure fluid is preferably not compressible, and a device for measuring the supplied amount of pressure fluid is provided. This makes it possible to control the degree of expansion through the supplied quantity.

In accordance with another advantageous embodiment of the invention, a monitoring device is provided which monitors changes over time of the fluid pressure and the supplied fluid quantity so that the pressure application can be interrupted when predetermined relative values of these changes are exceeded. Such a monitoring device prevents fluid which is under high pressure from being released into the body when the supporting implant is destroyed, for example, as a result of a material defect.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING

In the drawing:

FIG. 1 is a schematic sectional view of a device according to the invention with a supporting implant placed on a pressure line;

FIG. 2 is an illustration of a detail of the supporting implant of FIG. 1;

FIG. 5 is an illustration of another embodiment of the supporting implant which can be used in a device of the invention.

DETAILED DESCRIPTION OF THE INVENTION

Figure 3:
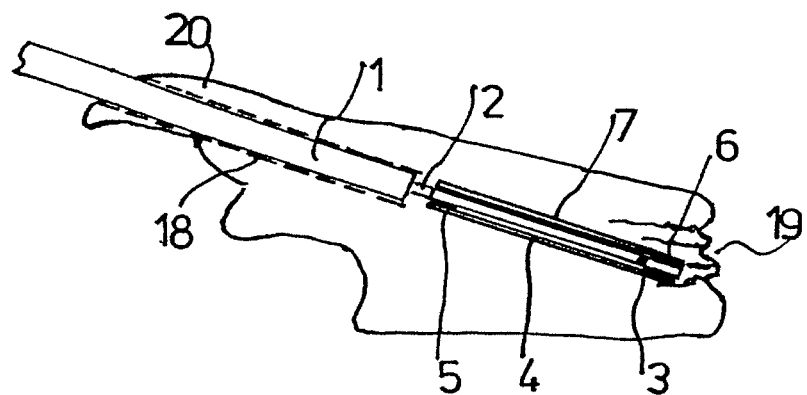
FIG. 3 is an illustration, on a smaller scale, showing the device of FIG. 1 inserted into a broken and compressed vertebral body.

FIG. 1 of the drawing shows a guide sleeve 1 and a pressure line 2 extending through the guide sleeve 1, wherein the pressure line 2 is provided with an opening 3 for releasing a pressure fluid.

An elastic hose-type sheath 4 is placed in the manner of a stocking and flush at the ends thereof on the circular cylindrical pressure line 2. The sheath 4 is glued in a pressure-tight manner at its ends to the circumference of the pressure line 2 at 5 and 6. Instead of providing a glued connection, it would also be possible to press the elastic sheath 4 at the ends thereof by means of rings against the pressure line.

A hollow-cylindrical supporting implant 7 is placed around the elastic sheath 4. As can be seen in FIG. 2, the cylindrical wall 8 of the implant 7 is a mesh-like material with openings 9, wherein wires of the mesh extend at an acute angle relative to each other. The wall 8 can be tangentially expanded in the manner of expanded metal in the direction of double arrow 21, so that the supporting implant 7 is radially expanded.

At its end opposite the sheath 4 or the supporting implant 7, the pressure line 2 is in connection with a schematically illustrated device 10 for supplying an incompressible pressure fluid 11, wherein this device 10 includes a pressure cylinder 12 and a piston 13. The piston 13 may be movable manually, preferably by means of a screw-type pressure gauge, or by means of a motor drive.

Reference numeral 14 denotes a schematically illustrated control and monitoring device which includes a pressure indicator 16 and a display 17 for the supplied quantity of pressure fluid.

The manner of operation of the device is shown in FIGS. 1 and 2 and shall now be explained in connection with FIGS. 3 and 4.

For stabilizing a broken vertebra, initially a duct 18 is drilled through the pedicle 20, wherein a catheter and a drilling tool extending through the catheter can be used for this purpose. As shown in FIGS. 3 and 4, the guide sleeve 1 is now placed in the duct 18 and the pressure fluid 2 with the supporting implant 7 can be forwardly pushed into the interior of the compressed vertebra which has compression folds at 19.

The incompressible pressure fluid 11 is pressed by means of the device 10 into the pressure line 2, the pressure fluid 11 emerges from the opening 3 and the elastic sheath 4 is expanded into a balloon. The expanding sheath or balloon 4 expands the supporting implant 7, as illustrated in FIG. 4, wherein the wall 8 of the supporting implant 7 is plastically deformed in the direction of arrow 21 shown in FIG. 2 and the acute angles between the mesh wires at 17 are widened.

The quantity of supplied pressure fluid during the expansion can be read at the display 15 of the control and monitoring device 14 and, thus, the extent of the achieved expansion can be determined. The expansion or supply of pressure fluid is stopped when a predetermined value of the supplied pressure fluid quantity has been reached.

The control and monitoring device 14 further ensures that the application of pressure is stopped immediately if the balloon 4 ruptures during the expansion, for example, due to a material defect, and pressure fluid is released from the vertebra; this is the case when the supplied pressure fluid quantity increases significantly over time, while the pressure stays constant or increases only slightly.

After the required expansion has been achieved, the pressure fluid is withdrawn through the opening 3 which is located near the lowest point of the balloon 4. The pressure line 2 with the empty pressure balloon or the empty sheath 4 can now be pulled back through the guide sleeve 1.

Figure 4:
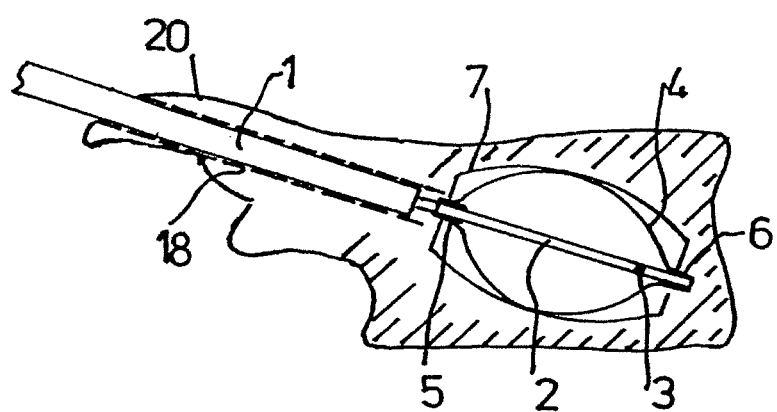
FIG. 4 shows the vertebral body of FIG. 3 which has been expanded by means of the device of FIG. 1.

The plastically deformed supporting implant 7 maintains its shape and supports the vertebra in such a way that it maintains the shape shown in FIG. 4 and the damage shown at 19 can heal. A filler material is introduced into the interior of the supporting implant.

FIG. 2 is a cross-sectional view of another embodiment of a supporting implant 7a according to the invention. The supporting implant 7a has in its wall 8a folds 22, wherein the folds on opposite sides have different lengths, so that the expanded implant has a rectangular shape in cross-section.

In the embodiment described above, a salt solution containing an x-ray contrast agent is used as the pressure fluid.

Of course, two of the above-described supporting implants can be and are usually inserted into a broken vertebra, wherein ducts are drilled in both pedicles for inserting a catheter.

While specific embodiments of the invention have been shown and described in detail to illustrate the inventive principles, it will be understood that the invention may be embodied otherwise without departing from such principles.

I claim:

1. A method of stabilizing a patient's vertebral column by stabilizing a broken vertebra utilizing a hollow-cylindrical, plastically deformable supporting implant and a pressure balloon mounted to a pressure line, the method comprising the steps of:
   (a) making an incision in the patient's skin;
   (b) forming a duct through a cortical portion of the broken vertebra to access an interior cancellous portion of the vertebra;
   (c) inserting the pressure line, pressure balloon and plastically deformable supporting implant through the duct and into the interior cancellous portion of the vertebra, wherein the plastically deformable supporting implant comprises a wire mesh comprising openings, and wherein the wires of the mesh extend at an acute angle relative to each other;
   (d) injecting fluid into the pressure balloon and the pressure line to create an internal pressure in the pressure balloon and expand the pressure balloon, expansion of the pressure balloon causing the plastically deformable supporting implant to plastically deform from an initial, non-expanded state to an expanded state so that a hollow space is formed in the interior cancellous portion of the patient's vertebra and endplates of the vertebra are urged away from each other to generally return the broken vertebra to its original shape, wherein in the expandable state the acute angles of the mesh wires are widened;
   (e) constantly monitoring the internal pressure in step (d);
   (f) stopping the fluid injection of step (d) when a predetermined value of the internal pressure is reached;
   (g) withdrawing the fluid from the pressure balloon and the pressure line;
   (h) removing the pressure balloon and pressure line from the interior cancellous portion of the vertebra and the duct, thereby leaving the plastically deformed supporting implant within the vertebra in the expanded state to maintain the shape of the implant and support the vertebra to allow the broken vertebra to heal; and
   (i) closing the incision.

2. The method of claim 1, wherein the fluid is comprised of an incompressible salt solution containing an x-ray contrasting agent.

3. The method of claim 1, wherein the duct in step (b) is formed through a pedicle of the vertebra.

4. The method of claim 1, comprising the further step of: inserting a guide sleeve down the duct of step (b).

5. The method of claim 1, wherein the duct of step (b) is comprised of a first duct drilled in a first pedicle and a second duct drilled in a second pedicle of the vertebra.

6. The method of claim 5 comprising the further step of: simultaneously inserting a first pressure balloon, first pressure line and first plastically deformable supporting implant through the first duct and into hollow space and inserting a second pressure balloon, second pressure line and second plastically deformable supporting implant through the second duct and into the hollow space.

7. The method of claim 1, further comprising the step of: inserting a guide sleeve through the duct for receiving the pressure line, pressure balloon and plastically deformable supporting implant therethrough.

8. The method of claim 1 wherein the internal pressure in step (e) is monitored utilizing a control and monitoring device that includes a display indicating a supplied quantity of the fluid injected in step (d) and a pressure indicator.

9. The method of claim 8 comprising the further step of: immediately stopping the injection of step (d) utilizing the control and monitoring device if the balloon ruptures.

10. The method of claim 1, further comprising the step of introducing a filler material into the supporting implant in the expanded state subsequent to step (h).

11. A method of stabilizing a patient's vertebral column by stabilizing a broken vertebra utilizing a hollow-cylindrical, plastically deformable, expandable supporting implant and a pressure balloon mounted to a pressure line, wherein the plastically deformable, expandable supporting implant comprises a wire mesh comprising openings, and wherein the wires of the mesh extend at an acute angle relative to each other, the method comprising the steps of:

(a) causing the plastically deformable, expandable supporting implant to plastically expand from a non-expanded state to an expanded state by application of an internal pressure thereto utilizing the pressure balloon such that the acute angles of the mesh wires are widened;

(b) removing the pressure balloon from within the supporting implant in the expanded state wherein the plastically deformed supporting implant within the vertebra in the expanded state maintains the shape of the implant and supports the vertebra to allow the broken vertebra to heal;

(d) monitoring changes over time of at least one of pressure and quantity of a fluid used to apply the internal pressure utilizing a monitoring device; and (e) automatically ceasing application of the internal pressure if predetermined relative values of the changes are exceeded.

12. The method of claim 11, wherein the supporting implant is constructed of a metal mesh.

13. The method of claim 11, further comprising the step of introducing a filler material into the supporting implant in the expanded state subsequent to step (b).

* * * * *